United States Patent [19]
Wei

[11] Patent Number: 6,139,150
[45] Date of Patent: Oct. 31, 2000

[54] COMPACT VISUAL FIELD TESTER

[75] Inventor: Jay Wei, Fremont, Calif.

[73] Assignee: Carl Zeiss, Inc., Thornwood, N.Y.

[21] Appl. No.: 09/235,249

[22] Filed: Jan. 22, 1999

[51] Int. Cl.[7] .................................................. A61B 3/10
[52] U.S. Cl. ............................................................ 351/211
[58] Field of Search .................................. 351/210, 211, 351/212, 213, 214, 215; 345/8, 9; 359/629, 630

[56] References Cited

U.S. PATENT DOCUMENTS

| | | | |
|---|---|---|---|
| 4,397,531 | 8/1983 | Lees ......................................... | 351/210 |
| 4,561,738 | 12/1985 | Humphrey et al. ...................... | 351/226 |
| 5,046,835 | 9/1991 | Billeter et al. ........................... | 351/206 |
| 5,418,584 | 5/1995 | Larson ..................................... | 351/122 |
| 5,491,524 | 2/1996 | Hellmuth et al. ....................... | 351/212 |
| 5,808,589 | 9/1998 | Fergason ................................. | 345/8 |

*Primary Examiner*—George Manuel
*Attorney, Agent, or Firm*—Michael B. Einschlag

[57] ABSTRACT

A visual field tester which measures the visual field of a patient's eye, which visual field tester includes: (a) an optical radiation source having an entrance pupil plane, which optical radiation source outputs one or more spots of optical radiation; and (b) an optical relay system which relays a point in the entrance pupil plane or a point conjugate to the point in the entrance pupil plane to the patient's eye with a one-to-one magnification, wherein the optical relay system comprises a beamsplitter disposed at an angle with respect to a retroreflector array.

14 Claims, 3 Drawing Sheets

COMPACT VISUAL FIELD TESTER

TECHNICAL FIELD OF THE INVENTION

The present invention pertains to a visual field tester and, in particular, to a compact visual field tester.

BACKGROUND OF THE INVENTION

The testing of visual functions includes perimetry, determination of sharpness of visual perception on the retina, determination of flicker frequency, determination of contrast sensitivity, and color contrast sensitivity. Apparatus which can carry out such tests are called automatic perimeters or visual field testers and have been known in the art for many years.

In prior art visual field testers, it is common to include a hemispherical projection surface and to place a patient's eye at or close to the center of the hemisphere for testing. The tested eye is directed toward the apex of the hemisphere and, in particular, toward the apex of the internal surface of the hemisphere while the patient is directed to a central fixation illumination. A projector presents stimuli at selected points of the internal surface of the hemisphere for example, by sequentially flashing images of light sources on the internal surface of the hemisphere. In response, the patient generates signals for example, by pressing a button to indicate detection or non-detection of the stimuli. Typically, a computer receives the signals and generates the patient's visual field, which visual field is used to plot the absence, presence, and/or progress of disease. A drawback of such prior art, indirect illumination visual testers is that they are bulky and expensive. For example, in order for the patient to look directly at the internal surface of the hemisphere, the minimum distance of the internal surface from the eye must be at least 30 cm. The size of the hemisphere for a 60 degree field of view at a distance of 30 cm is 30 cm in diameter. As a rule, the diameter of the hemisphere is in a range of 60–100 cm. Further, the center of the hemisphere is normally located at eye level of the patient who is typically seated during the test procedure. Therefore, the overall height of such a prior art visual field tester is necessarily in the range of two meters.

An improvement on the above-described prior art visual field tester is disclosed in U.S. Pat. No. 5,046,835 (the '835 patent). In particular, the '835 patent discloses an apparatus used to test visual functions of a patient's eye that occupies only a fraction of the space taken up by a conventional apparatus such as that described above. In particular, the '835 patent discloses an apparatus which provides stimuli at finely spaced intervals which is comprised of a radiation source, stimuli presenting means in the form of a diaphragm (the diaphragm is disposed between the radiation source and the patient's eye), an eyepiece including one or more optical elements (the eyepiece is disposed between the diaphragm and the patient's eye), and a collection lens for producing real, intermediate images of the stimuli from the diaphragm (the collection lens is disposed in a plane between the plane of the aperture of the diaphragm and the eyepiece). The purpose of the eyepiece is to provide sharp images of the real, intermediate images upon the retina of the eye. As disclosed in the '835 patent, the apparatus further comprises a computer to set the intensity of the radiation output as a function of time. Further, as shown in FIG. 2 and as described at col. 6 of the '835 patent, an assembly 22 which includes the radiation source is movable at right angles to the optic axis of the lens of the patient's eye by a computer-controlled drive. This enables the diaphragm to move its aperture in a plane disposed at right angles to the optic axis to enable stimuli to be presented at any desired point of the plane. The coordinates of locations of successively presented stimuli are selected by the computer in accordance with a predetermined program.

A need exists in the art for a method and apparatus for testing the visual field of a patient with a compact visual field tester and, preferably, a visual field tester that projects test spots directly into the patient's eye without vignetting.

SUMMARY OF THE INVENTION

Embodiments of the present invention advantageously provide method and apparatus for testing the visual field of a patient without vignetting for all fields using a compact visual field tester. In particular, an embodiment of the present invention is a compact visual field tester that projects test spots directly into the patient's eye. Advantageously, in accordance with the present invention, the compact visual field tester: (a) projects test spots directly into the patient's eye without vignetting for all fields; (b) has a working distance that is long enough (i.e., test spots are placed at optical infinity) to be comfortable for the patient (i.e., the patient can be relaxed in accommodation during testing, which relaxation in accommodation enhances test accuracy); (c) has an entrance pupil for the optical system that is large enough to accommodate the patient's eye movement (the large entrance pupil results because the lens aperture is directly relayed to the eye pupil so that the lens aperture defines the size of the entrance pupil); (d) has a compact optical system which enables the field tester to be placed close to the patient's eye; and (e) has an optical system that can be adjusted to accommodate the patient's refraction so that a "trial" lens is not needed (a trial lens is used to adjust the patient's refraction during testing).

An embodiment of the present invention is a visual field tester which measures the visual field of a patient's eye, which visual field tester comprises: (a) an optical radiation source having an entrance pupil plane, which optical radiation source outputs one or more spots of optical radiation; and (b) an optical relay system which relays a point in the entrance pupil plane or a point conjugate to the point in the entrance pupil plane; wherein the optical relay system comprises a beamsplitter disposed at an angle with respect to a retroreflector.

DETAILED DESCRIPTION

It is known in the art that a patient's eye can be placed at the entrance pupil plane of an optical system to enable the patient to see the full field of view without vignetting. However, for most prior art projection lenses, the entrance pupil plane is either inside a lens group or at a first lens of the lens group. As is known, it is physically impossible to place the patient's eye at the entrance pupil plane of such prior art projection lenses. To solve this problem, one can utilize a projection lens which has an entrance pupil plane in front of the projection lens. However, as is known, such a projection lens becomes large and lateral color aberration for such a lens will be worse when the distance of the entrance pupil plane in front of the lens is increased. Further, such lateral color aberration is difficult to correct without using exotic and expensive glass materials. Thus, it is known that one way to overcome the above-described problem is to use an optical relay system that images the entrance pupil plane in a plane in open space so that the patent's eye can be placed at that plane.

Figure 1:
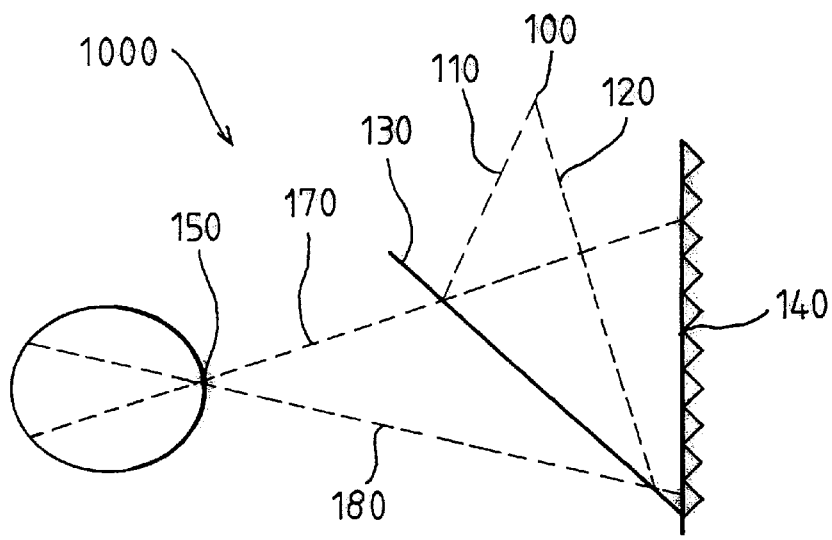
FIG. 1 shows a diagram of an embodiment of an optical relay system used to fabricate embodiments of the present invention.

FIG. 1 shows a diagram of an embodiment of inventive optical relay system 1000 that images an entrance pupil in a plane in open space, which optical relay system 1000 is used to fabricate a compact visual field tester in accordance with the present invention. As shown in FIG. 1, and in accordance with the present invention, a patient's eye is placed at the image of the entrance pupil plane of an optical projection system (not shown in FIG. 1) to enable the patient to see a full field of view without vignetting.

In FIG. 1, for ease of understanding the principles of the present invention, the optical projection system is represented by the location of its entrance pupil plane. As shown in FIG. 1, dotted lines 110 and 120 that emanate from point 100 in the entrance pupil plane of the optical projection system are chief rays of the optical projection system. Optical radiation emanating from point 100 impinges upon beamsplitter 130 and a portion of the optical radiation is reflected toward retroreflector array 140. As is well known to those of ordinary skill in the art, a retroreflector is an apparatus comprised of three (3) mirrors that are located substantially at 90 degrees to each other to form a corner cube type reflector. As is also well known to those of ordinary skill in the art, for a large range of incident angles, a retroreflector reflects an optical beam back at the same angle at which the optical beam was incident upon the retroreflector.

As shown in FIG. 1, optical radiation directed toward retroreflector array 140 is reflected by the micro-corner cubes of retroreflector array 140 at the same angle at which the optical radiation was incident thereupon. A portion of the optical radiation reflected by retroreflector array 140 passes through beamsplitter 130 and impinges upon point 150 which is the image of point 100 in the entrance pupil plane of the optical projection system. In accordance with the present invention, and as shown by dotted lines 170 and 180, all optical radiation that emanates from point 100 in the entrance pupil plane will converge to point 150. Whenever the distance between point 100 and beamsplitter 130 and the distance between point 150 and beamsplitter 130 are equal, optical relay system 1000 is a one-to-one optical relay system without optical aberration. As will be described in detail below, optical relay system 1000 is used to fabricate embodiments of the present invention wherein the patient's eye is placed so that a pupil is at point 150. It should be clear to those of ordinary skill in the art that the angle between beamsplitter 130 and retroreflector array 140 do not have to be any particular angle such as, for example, 45°. The angle may be any amount, subject to the need to provide comfort for the patient being tested. Further, it should be clear to those of ordinary skill in the art that the size of the retroreflectors which comprise retroreflector array 140 should be small and is determined primarily by the amount of displacement of the incident ray one can tolerate in designing the optical relay system. Still further, it should be clear to those of ordinary skill in the art that embodiments of the present invention may be fabricated utilizing any device that has substantially the same property of retroreflector array 140 wherein incident rays are reflected at the same angle at which the rays were incident thereupon.

Figure 2:
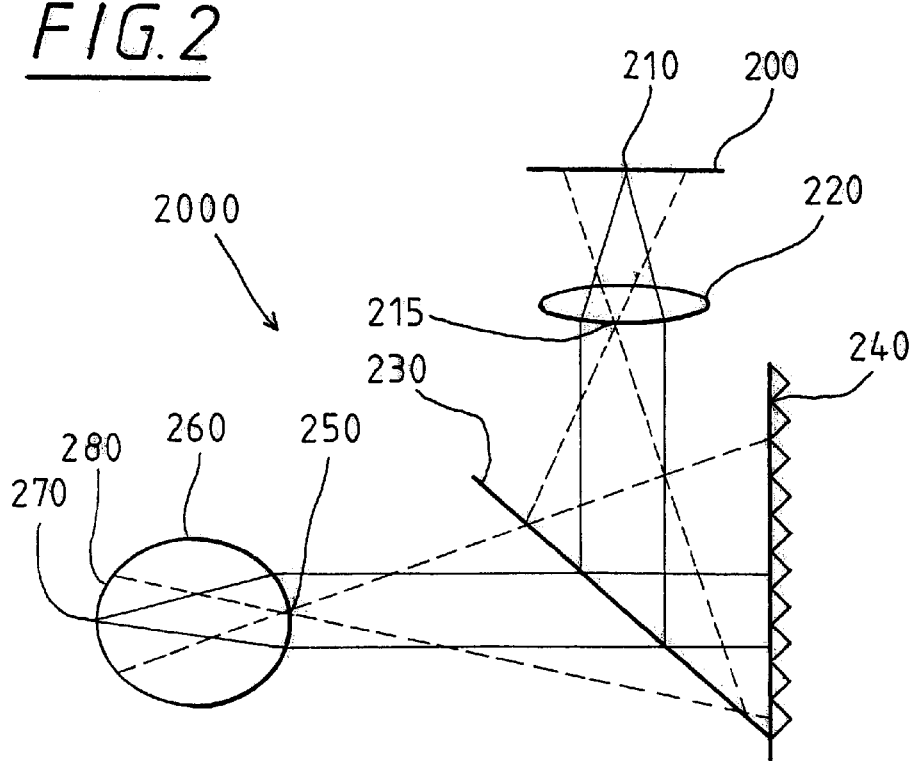
FIG. 2 shows a diagram of a first optical configuration used to fabricate a compact visual field tester in accordance with the present invention, which optical configuration includes the optical relay system shown in FIG. 1.

FIG. 2 shows a diagram of optical configuration 2000 used to fabricate a compact visual field tester in accordance with the present invention, which optical configuration 2000 includes optical relay system 1000 shown in FIG. 1. As shown in FIG. 2, array 200 is an array of light emitting diodes (LEDs) or an array of individually illuminated spots, which array 200 is controlled, for example, by a controller in the form, for example, of a computer (not shown). A visual field tester is fabricated in accordance with the present invention by providing an interface apparatus (not shown) between the controller and array 200 in a manner which is well known to those of ordinary skill in the art. Then, in accordance with methods which are well known to those of ordinary skill in the art, for example, under software control, the controller sends signals through the interface to array 200 to cause various elements in array 200 to emit optical radiation. For example, it well known how to control individual elements of an LED array utilizing a computer. Further, in accordance with methods that are well known to those of ordinary skill in the art, the controller, under software control, controls illumination of the elements of array 200 by: (a) element position; (b) sequence of illumination; (c) duration of illumination interval; (d) intensity of illumination during the illumination interval; and (e) even color. Similarly, it is well known to those of ordinary skill in the art how array 200 may be fabricated using individual light sources other than LEDs which emit radiation through masks or by using a single light source to illuminate a number of individually, computer-controlled masks arranged in an array.

As shown in FIG. 2, optical radiation emanating from point 210 in array 200 impinges upon lens system 220 (shown in FIG. 2 as a single lens for ease of understanding the invention). Lens system 220 has a focal length f and array 200 is placed in the focal plane of lens system 220. As a result, the optical radiation emanating from point 210 of array 200 which impinges upon lens system 220, emerges as a bundle of parallel rays that impinge upon beamsplitter 230. Point 215 is in the entrance pupil plane of lens system 210. As further shown in FIG. 2, optical relay system 1000 described above in conjunction with FIG. 1 is used to fabricate embodiment 2000. As was the case for FIG. 1, the dotted lines in FIG. 2 show the chief rays of lens system 220. As was described above in conjunction with FIG. 1, the use of beamsplitter 230 and retroreflector array 240 causes point 215 in the entrance pupil plane of lens system 210 to be conjugated with point 250 on the pupil of eye 260.

In particular, the optical radiation reflected from beamsplitter 230 towards retroreflector array 240 is reflected back through beamsplitter 230 and a portion impinges upon the pupil of eye 260. As shown, in FIG. 2, the optical radiation is then focused by eye 260 to spot 270 on retina 280. The size of spot 270 is determined by a magnification factor $f/f_{eye}$ where $f_{eye}$ is the focal length of eye 260. Advantageously, in accordance with the present invention, the size of the entrance pupil of lens system 220 has not changed and there is no vignetting.

Lastly, as is well known to those of ordinary skill in the art, in order to fabricate a visual field tester in accordance with the present invention, the patient is provided with an apparatus for indicating the patient's perception of the presence or absence of optical radiation impinging upon the eye. As is well known, such indication apparatus includes a button which, when depressed, sends a signal to the controller. Such an indication apparatus may also include foot pedals, mouses and the like. Further, the inventive visual field tester may include a fixation device which engages the attention of the tested eye and which may be fabricated in accordance with any one of a number of methods that are well known to those of ordinary skill in the art. For example, a fixation device may be an LED which is disposed at a predetermined location for viewing by the patient's tested eye. Lastly, the controller may be configured in accordance with any one of a number methods which are well known to those of ordinary skill in the art to collect the patient's input to produce, as output, measurements of the patient's visual sensitivity.

Figure 3:
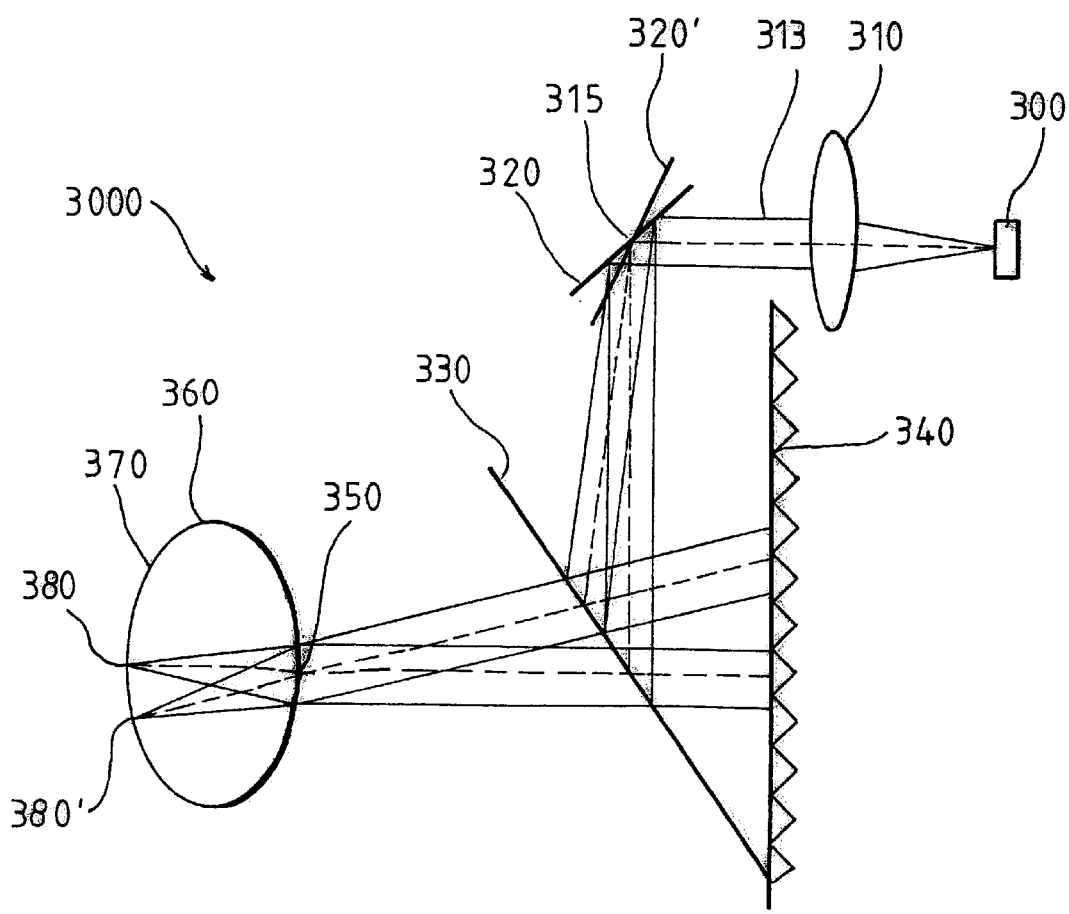
FIG. 3 shows a diagram of a second optical configuration used to fabricate a compact visual field tester in accordance with the present invention, which optical configuration includes the optical relay system shown in FIG. 1.

FIG. 3 shows a diagram of optical configuration 3000 used to fabricate a compact visual field tester in accordance with the present invention, which optical configuration includes optical relay system 1000 shown in FIG. 1. As shown in FIG. 3, optical configuration 3000 comprises a single source of optical radiation 300 and a scanner 320 instead of array 200 utilized in accordance with optical configuration 2000 which was described above in conjunction with FIG. 2. As shown in FIG. 3, optical radiation source 300 is disposed in the back focal plane of lens system 310 (shown in FIG. 3 as a single lens for ease of understanding the invention). Optical radiation source 300 may be an LED or it may be any other source of optical radiation having a predetermined spot size. A visual field tester is fabricated in accordance with the present invention by providing an interface apparatus (not shown) between a controller, for example, a computer (not shown) and optical radiation source 300. Then, in accordance with methods which are well known to those of ordinary skill in the art, for example, under software control, the controller sends signals through the interface to optical radiation source 300 to cause it to emit optical radiation. For example, it is well known how to control an LED utilizing a computer. Further, in accordance with methods that are well known to those of ordinary skill in the art, the controller, under software control, controls output from optical radiation source 300 as to: (a) duration of illumination interval; (b) intensity of illumination during the illumination interval; and (c) even color.

As shown in FIG. 3, optical radiation emitted from optical radiation source 300 impinges upon lens system 310 and emerges as parallel beam 313. Parallel beam 313 impinges upon scanner 320 which is placed substantially at point 315, which point 315 is disposed in the entrance pupil plane of lens system 310. In FIG. 3, scanner 320 is shown in a first position (indicated by 320) and a second position (indicated by 320'). As further shown in FIG. 3, optical relay system 1000 described above in conjunction with FIG. 1 is used to fabricate embodiment 3000. As was the case for FIG. 1, the dotted lines in FIG. 3 show the chief rays of lens system 310. As was described above in conjunction with FIG. 1, the use of beamsplitter 330 and retroreflector array 340 causes point 315 in the entrance pupil plane of lens system 310 to be conjugated with point 350 on the pupil of eye 360.

In particular, the optical radiation reflected by scanner 320 impinges upon beamsplitter 330 and a portion of the optical radiation is reflected from beamsplitter 330 and directed to impinge upon retroreflector array 340. Next, optical radiation impinging upon retroreflector array 340 is reflected back toward beamsplitter 330. A portion of the optical radiation then passes through beamsplitter 330 and impinges upon the pupil of eye 360. Finally, eye 360 focuses the optical radiation onto retina 370. Since point 315 is conjugate to the pupil of eye 360, no vignetting is introduced for a large angle scan of scanner 320. As shown in FIG. 3, point 380 on retina 370 corresponds to scanner position 320 and point 380' on retina 370 corresponds to scanner position 320'.

The visual field tester is fabricated in accordance with the present invention by providing an interface apparatus (not shown) between the controller and scanner 320 in a manner which is well known to those of ordinary skill in the art. Then, in accordance with methods which are well known to those of ordinary skill in the art, for example, under software control, the controller sends signals through the interface to cause scanner 320 to rotate and, thereby, to scan the optical radiation incident thereon from optical radiation source 300. As scanner 320 scans, optical radiation output from optical radiation source 300 is scanned over different locations on the patient's retina.

Many methods are well known to those of ordinary skill in the art for fabricating scanner 320. For example, scanner 320 may be fabricated by affixing a mirror to a galvanically activated motor, which motor is interfaced to the controller in a manner that is well known to those of ordinary skill in the art. Further, it is well known to those of ordinary skill in the art how to control the scan position of scanner 320 under software control.

As those of ordinary skill in the art can readily appreciate, for scanning in both the horizontal and vertical direction, one needs two scanners. However, since horizontal and vertical scanners cannot be physically placed at the same point, in fabricating embodiments of the present invention, scanners are placed at images of the front and back pupil planes whereby they are separated by a short distance.

Lastly, as is well known to those of ordinary skill in the art, in order to fabricate a visual field tester in accordance with the present invention, the patient is provided with an apparatus for indicating the patient's perception of the presence or absence of optical radiation impinging upon the eye. As is well known, such indication apparatus includes a button which, when depressed, sends a signal to the controller. Such an indication apparatus may also include foot pedals, mouses and the like. Further, the inventive visual field tester may include a fixation device which engages the attention of the tested eye and which may be fabricated in accordance with any one of a number of methods that are well known to those of ordinary skill in the art. For example, a fixation device may be an LED which is disposed at a predetermined location for viewing by the patient's tested eye. Lastly, the controller may be configured in accordance with any one of a number methods which are well known to those of ordinary skill in the art to collect the patient's input to produce, as output, measurements of the patient's visual sensitivity.

Figure 4:
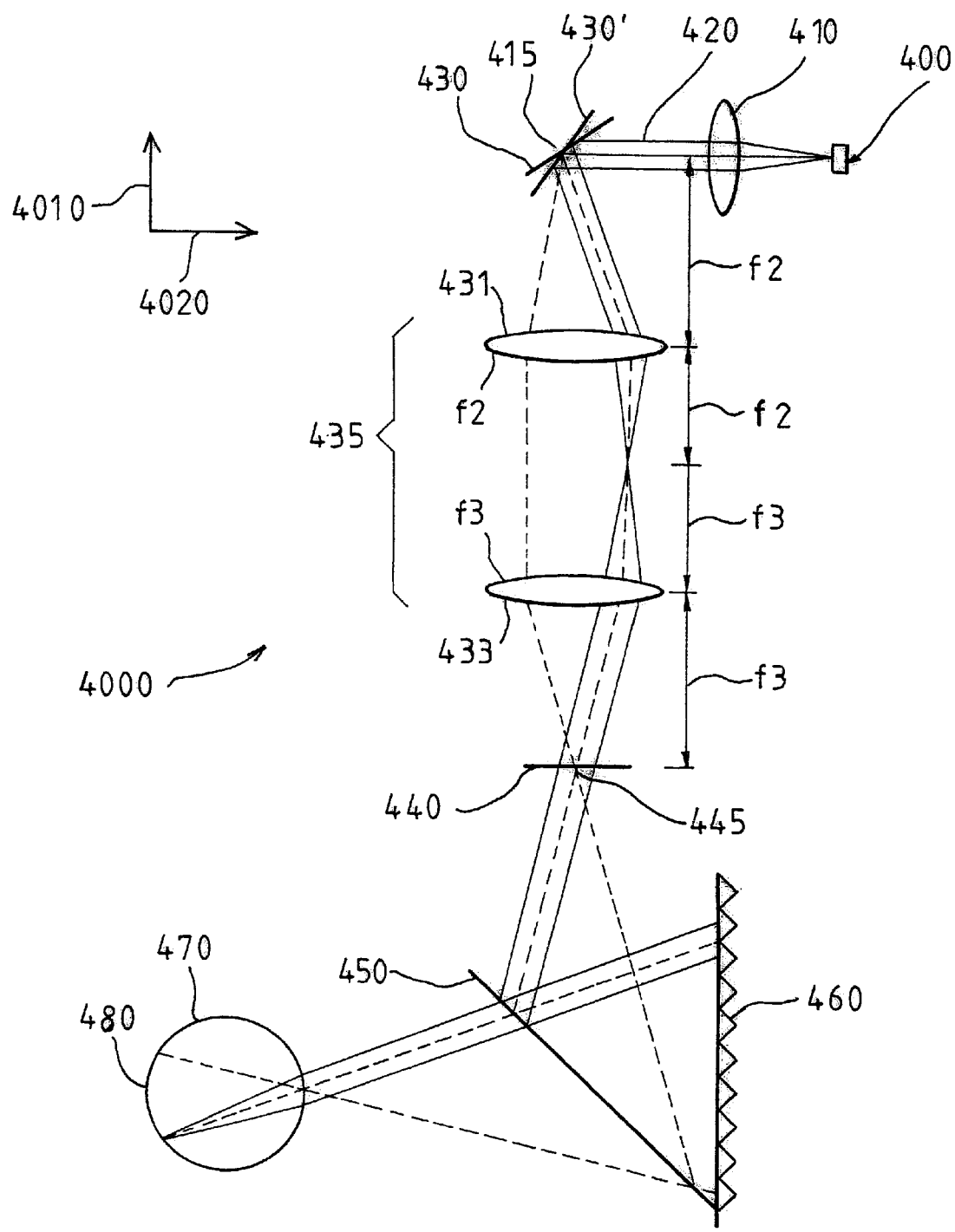
FIG. 4 shows a diagram of a third optical configuration used to fabricate a compact visual field tester in accordance with the present invention, which optical configuration includes the optical relay system shown in FIG. 1.

FIG. 4 shows a diagram of optical configuration 4000 used to fabricate a compact visual field tester in accordance with the present invention, which optical configuration includes optical relay system 1000 shown in FIG. 1. Embodiment 4000 eliminates the problem presented by embodiment 3000 wherein two scanners need to be placed at the same point, which point is conjugate to the patient's pupil. The problem is solved by embodiment 4000 wherein the entrance pupil plane of a lens system is first relayed through a relay lens system having magnification equal to one and is then relayed again using the optical relay system shown in FIG. 1. In such an embodiment there are two conjugates planes for the patient's pupil and, as a result, a horizontal scanner is placed at one of the conjugate planes and a vertical scanner is placed at the second conjugate plane. Again, dotted lines show the chief rays.

As shown in FIG. 4, optical configuration 4000 comprises a single source of optical radiation 400 and a scanner 430. As further shown in FIG. 4, optical radiation source 400 is disposed in the back focal plane of lens system 410 (shown in FIG. 4 as a single lens having a focal length $f_1$ for ease of understanding the invention). Optical radiation source 400 may be an LED or it may be any other source of optical radiation having a predetermined spot size. A visual field tester is fabricated in accordance with the present invention by providing an interface apparatus (not shown) between a controller, for example, a computer (not shown) and optical radiation source 400. Then, in accordance with methods which are well known to those of ordinary skill in the art, for example, under software control, the controller sends signals through the interface to optical radiation source 400 to cause it to emit optical radiation. For example, it is well known how to control an LED utilizing a computer. Further, in accordance with methods that are well known to those of ordinary skill in the art, the controller, under software control, controls output from optical radiation source 400 as to: (a) duration of illumination interval; (b) intensity of illumination during the illumination interval; and (c) even color.

As shown in FIG. 4, optical radiation emitted from optical radiation source 400 impinges upon lens system 410 and emerges as parallel beam 420. Parallel beam 420 impinges upon scanner 430 which is placed substantially at point 415, which point 415 is disposed in the entrance pupil plane of lens system 410. In FIG. 4, scanner 430 is shown in a first position (indicated by 430) and a second position (indicated by 430').

The visual field tester is fabricated in accordance with the present invention by providing an interface apparatus (not shown) between the controller and scanner 430 in a manner which is well known to those of ordinary skill in the art. Then, in accordance with methods which are well known to those of ordinary skill in the art, f6r example, under software control, the controller sends signals through the interface to cause scanner 430 to rotate and, thereby to scan the optical radiation incident thereon from optical radiation source 400. As scanner 430 scans, optical radiation output from optical radiation source 400 is scanned over different locations on the patient's retina. For embodiment 4000, the plane of FIG. 4 will be taken as the y-z plane (as shown by arrows 4010 and 4020). Scanner 430 in FIG. 4 rotates about the x-axis which is perpendicular to the plane of FIG. 4.

The optical radiation reflected by scanner 430 impinges upon relay lens system 435 having a magnification of one-to-one. As shown in FIG. 4, relay lens system 435 comprises lens system 431 (shown in FIG. 4 as a single lens having focal length $f_2$ for ease of understanding the present invention) and lens system 433 (shown in FIG. 4 as a single lens having focal length $f_3$ for ease of understanding the present invention). Scanner 430 is placed in the back focal plane of lens system 431, substantially at a distance equal to focal length $f_2$. The output from relay system 435 is a parallel beam and the parallel beam is directed, in turn, to impinge upon scanner 440. Scanner 440 is disposed to rotate about point 445 which is conjugate to point 415.

The visual field tester is fabricated in accordance with the present invention by providing an interface apparatus (not shown) between the controller and scanner 440 in a manner which is well known to those of ordinary skill in the art. Then, in accordance with methods which are well known to those of ordinary skill in the art, for example, under software control, the controller sends signals through the interface to cause scanner 440 to rotate and, thereby, to scan the optical radiation incident thereon from relay lens system 435. As scanner 440 scans, optical radiation output from relay lens system 435 is scanned over different locations on the patient's retina. Scanner 440 in FIG. 4 rotates about the y-axis.

As further shown in FIG. 4, optical relay system 1000 described above in conjunction with FIG. 1 is used to fabricate embodiment 4000. In particular, the optical radiation reflected by scanner 440 impinges upon beamsplitter 450 and a portion of the optical radiation is reflected from beamsplitter 450 and directed to impinge upon retroreflector array 460. Next, optical radiation impinging upon retroreflector array 460 is reflected back toward beamsplitter 450. A portion of the optical radiation then passes through beamsplitter 450 and impinges upon the pupil of eye 470. Finally, eye 470 focuses the optical radiation onto retina 480. Since points 415 and 445 are conjugate to the pupil of eye 470, no vignetting is introduced for large angle scans. The distance between scanner 440 and beamsplitter 450 is substantially equal to the distance between beamsplitter 450 and the corneal plane of eye 470. This distance is set so that the patient's movement does not cause interference with the system to provide a .degree of comfort for the patient.

Although embodiment 4000 has been fabricated using relay system 435, it should be understood by those of ordinary skill in the art that other relay systems may be used to fabricate embodiments of the present invention, including a relay system like embodiment 1000 described above.

Many methods are well known to those of ordinary skill in the art for fabricating scanners 430 and 440. For example, scanners 430 and 440 may be fabricated by affixing mirrors to galvanically activated motors, which motors are interfaced to the controller in a manner that is well known to those of ordinary skill in the art. Further, it is well known to those of ordinary skill in the art how to control the scan position of scanners 430 and 440 under software control.

Lastly, as is well known to those of ordinary skill in the art, in order to fabricate a visual field tester in accordance with the present invention, the patient is provided with an apparatus for indicating the patient's perception of the presence or absence of optical radiation impinging upon the eye. As is well known, such indication apparatus include a button which, when depressed, sends a signal to the controller. Such an indication apparatus may also include foot pedals, mouses and the like. Further, the inventive visual field tester may include a fixation device which engages the attention of the tested eye and which may be fabricated in accordance with any one of a number of methods that are well known to those of ordinary skill in the art. For example, a fixation device may be an LED which is disposed at a predetermined location for viewing by the patient's tested eye. Lastly, the controller may be configured in accordance with any one of a number methods which are well known to those of ordinary skill in the art to collect the patient's input to produce, as output, measurements of the patient's visual sensitivity.

Those skilled in the art will recognize that the foregoing description has been presented for the sake of illustration and description only. As such, it is not intended to be exhaustive or to limit the invention to the precise form disclosed.

What is claimed is:

1. A compact visual field tester for a patient's eye comprises:
   a radiation source having an entrance pupil plane, which radiation source includes an array of radiation sources, and which radiation source outputs one or more spots of optical radiation;
   an optical relay system which relays a point in the entrance pupil plane or a point conjugate to the point in the entrance pupil plane;
   an indication apparatus; and
   a controller adapted to control radiation sources of the array and to receive signals transmitted thereto from the indication apparatus in response to input from the patient;
   wherein the optical relay system comprises a beamsplitter disposed at an angle with respect to a retroreflector.

2. The compact visual field tester of claim 1 wherein the optical relay system has a magnification substantially equal to one-to-one.

3. The compact visual field tester of claim 2 wherein the optical relay system relays the point to a position substantially at which the patient's eye is located.

4. The compact visual field tester of claim 2 wherein the retroreflector is a retroreflector array.

5. The compact visual field tester of claim 4 wherein the array comprises an array of light emitting diodes.

6. The compact visual field tester of claim 4 wherein the array is disposed in the focal plane of a lens system.

7. A compact visual field tester for a patient's eye comprises:
   a source of a spot of radiation, a lens system, and one or more scanners, wherein the spot of radiation is disposed in a focal plane of the lens system and the one or more scanners are disposed to rotate substantially about a point in an entrance pupil plane of the lens system or a point conjugate to the point in the entrance pupil plane of the lens system;
   an optical relay system which relays a point in the entrance pupil plane or a point conjugate to the point in the entrance pupil plane;
   an indication apparatus; and
   a controller adapted to control radiation sources of the array and to receive signals transmitted thereto from the indication apparatus in response to input from the patient;
   wherein the optical relay system comprises a beamsplitter disposed at an angle with respect to a retroreflector.

8. The apparatus of claim 7 wherein the optical relay system has a magnification substantially equal to one-to-one and the retroreflector is a retroreflector array.

9. A compact visual field tester for a patient's eye comprises:
   a source of a spot of radiation, a first lens system, a first scanner, a relay system, and a second scanner, wherein:
   (a) the spot of radiation is disposed in a focal plane of the first lens system;
   (b) the first scanner is disposed to rotate substantially about a point in the entrance pupil plane of the first lens system or a first point conjugate to the point in the entrance pupil plane of the first lens system;
   (c) the relay system having a magnification of one-to-one disposed to relay the point in the entrance pupil plane of the first lens system or the first point to a point conjugate thereto; and
   (d) the second scanner disposed to rotate substantially about the conjugate point;
   an optical relay system which relays a point in the entrance pupil plane or a point conjugate to the point in the entrance pupil plane;
   an indication apparatus; and
   a controller adapted to control radiation sources of the array and to receive signals transmitted thereto from the indication apparatus in response to input from the patient;
   wherein the optical relay system comprises a beamsplitter disposed at an angle with respect to a retroreflector.

10. The apparatus of claim 9 wherein the optical relay system has a magnification substantially equal to one-to-one and the retroreflector is a retroreflector array.

11. A method for testing a visual field of a patient's eye which comprises the steps of:
    generating a spot of optical radiation which passes through an optical system having an entrance pupil plane;
    scanning the spot of radiation using a scanner disposed to rotate substantially about a point in the entrance pupil plane or a point conjugate to the point in the entrance pupil plane; and
    relaying using an optical relay system that relays a point in the entrance pupil or a point conjugate to the point in the entrance pupil;
    wherein the step of relaying comprises using an optical relay system that comprises a beamsplitter disposed at an angle with respect to a retroreflector.

12. The method of claim 11 wherein the optical relay system has a magnification substantially equal to one-to-one and the retroreflector is a retroreflector array.

13. A method for testing a visual field of a patient's eye which comprises the steps of:
    generating a spot of optical radiation which passes through an optical system having an entrance pupil plane;
    scanning the spot of radiation using a first scanner disposed to rotate substantially about a point in the entrance pupil plane or a first point conjugate to the point in the entrance pupil plane;
    relaying using a relay system having a magnification of one-to-one disposed to relay the point in the entrance pupil or the first point to a point conjugate thereto;
    scanning the spot using a second scanner disposed to rotate substantially about the conjugate point; and
    relaying using an optical relay system that relays a point in the entrance pupil or a point conjugate to the point in the entrance pupil; wherein the optical relay system comprises a beamsplitter disposed at an angle with respect to a retroreflector.

14. The method of claim 13 wherein the optical relay system has a magnification substantially equal to one-to-one and the retroreflector is a retroreflector array.

* * * * *